United States Patent [19]
Meier et al.

[11] Patent Number: 6,045,536
[45] Date of Patent: Apr. 4, 2000

[54] SECURING DEVICE FOR A LOW PROFILE GASTROSTOMY TUBE

[75] Inventors: Kevin C. Meier, St. Louis; Raymond O. Bodicky, Oakville, both of Mo.; Glenn Fournie, Smithton, Ill.; Alan Ranford, St. Louis, Mo.; Peter Von Dyck, Fernandina, Fla.

[73] Assignee: Sherwood Services, A.G., Schaffhausen, Switzerland

[21] Appl. No.: 09/257,164

[22] Filed: Feb. 24, 1999

[51] Int. Cl.[7] ........................................... A61M 5/32
[52] U.S. Cl. .................... 604/174; 128/DIG. 26; 606/108
[58] Field of Search ..................... 604/174, 175, 604/178, 179, 103–108, 264, 93; 128/DIG. 26; 606/108

[56] References Cited

U.S. PATENT DOCUMENTS

| | | | |
|---|---|---|---|
| 3,261,357 | 7/1966 | Roberts et al. | 128/348 |
| 3,794,041 | 2/1974 | Frei et al. | 128/348 |
| 3,814,080 | 6/1974 | Norman | 128/2 M |
| 4,944,732 | 7/1990 | Russo | 604/207 |
| 5,007,914 | 4/1991 | Schweigerling | 606/108 |
| 5,183,464 | 2/1993 | Dubrul et al. | 128/3 |
| 5,234,425 | 8/1993 | Fogarty et al. | 606/1 |
| 5,248,302 | 9/1993 | Patrick et al. | 604/178 |
| 5,267,983 | 12/1993 | Oilschlager et al. | 604/283 |
| 5,407,430 | 4/1995 | Peters | 604/104 |
| 5,456,699 | 10/1995 | Armstrong | 606/108 |

*Primary Examiner*—John D. Yasko
*Attorney, Agent, or Firm*—Lewis, Rice & Fingersh

[57] ABSTRACT

A low profile gastrointestinal tube feeding system having a securing device for securing a feeding set to a low profile gastrostomy tube thereof disposed inside the viscera of a patient's body so that inadvertent removal of the feeding set from the gastrostomy tube is prevented. The feeding set includes hollow tubing connected to a source of fluid at one end and a connection member at the other end for connection to the gastrostomy tube and establishing fluid flow communication with the patient. The low profile gastrostomy tube includes an external retention member having legs that seat and retain the external retention member against the patient's outer body and a tubular member that is disposed inside the stomach or other viscera of a patient. The connection member attaches to the external retention member and is secured thereto using a securing device. The securing device includes a top portion and a bottom portion which are adapted to simultaneously engage respective portions of the connection member and external retention member when the securing device is brought into sliding engagement thereto. The connection member is maintained in secure engagement with the external retention member through the securing device and neither part can be separated unless the securing device is first disengaged from either the connection member or external retention member. Thus, the securing device prevents inadvertent removal of the feeding set from the gastrostomy tube.

16 Claims, 12 Drawing Sheets

SECURING DEVICE FOR A LOW PROFILE GASTROSTOMY TUBE

BACKGROUND OF THE INVENTION

1. Field of the Invention

The present invention relates to a device for use with gastrointestinal-type tubes, and more particularly to a securing arrangement for use with low profile gastrointestinal feeding systems. More specifically, the present invention relates to a securing device for securing a feeding set to a low profile gastrostomy tube located outside the patient in order to prevent it inadvertent removal of the feeding set therefrom.

2. Prior Art

Low profile gastrointestinal feeding systems are frequently used for long term tube fed patients who are ambulatory and/or in a combative state and require some type of gastrostomy device to provide nutrition to a patient unable to take nutrition orally. These gastrointestinal systems comprise a feeding set attached to a source of nutrition at one end and a low profile gastrostomy tube at the other end. The low profile gastrostomy tube is normally inserted through a stoma formed in the patient's abdominal wall utilizing an internal retention member disposed inside a patient's viscera to anchor the free end of the gastrostomy tube inside the viscera. The internal retention member attaches to a distal or free end of the low profile gastrostomy tube to hold and affix a hollow organ of choice, e.g. the stomach, against the posterior abdominal wall of a patient. The hollow organ is so affixed by capturing the organ wall and abdominal wall between the internal retention member secured inside the organ and an external retention member seated on the outer abdominal wall outside a patient with a hollow tubular member attached between the respective retention members. The tubular member provides a fluid pathway between the feeding set connected to a source of nutrition and the internal retention member disposed inside the patient.

A typical internal retention member is disclosed in U.S. Pat. No. 5,248,302 to Patrick et al. entitled "Percutaneous obturatable Internal Anchoring Device" which describes a deformable obturatable internal retention member designed to pass through a stoma formed in a wall of the abdomen and stomach or other viscera of a patient in order to secure the low profile gastrostomy tube within the organ of choice and is herein incorporated by reference in its entirety. The method of using this type of obturatable internal retention member consists of inserting an obturator rod into the lumen of the low profile gastrostomy tube until the rod abuts or engages the distal end of the internal retention member. The internal retention member comprises a plurality of flexible retaining arms attached to the hollow tubular member that mechanically elongate and thereby slenderize the silicone, latex or polyurethane retaining arms to a size about that of the diameter of the tubular member when the obturator rod is pushed axially toward the patient. Such slenderization of the retaining arms allows safe insertion or removal of the tubular member and internal retention member into or from an established, matured stoma of a patient. Such obturatable internal retention members are currently the most common means used to insert, anchor and secure the low profile gastrostomy tube in a matured stoma of a patient.

After the internal retention member has been inserted inside the stomach, the obturator rod is withdrawn through the tubular member which allows the flexible retaining arms of the internal retention member to assume its preset enlarged shape, thereby retaining the internal retention member inside the stomach so that it cannot be withdrawn back through the stoma. Once the internal retention member assumes its preset enlarged shape the feeding tube with a connection member at one end is attached to the external retention member of the low profile gastrostomy tube in order to establish fluid flow communication between the source of nutrition and the patient's stomach. In this way, nutrition is provided to the patient through the low profile gastrostomy tube. Unfortunately, fluid flow communication between the source of nutrition and the patient may be interrupted by inadvertent removal of the feeding tube from the connection member by a patient in a combative state or a person passing too close to the feeding set, thereby creating a critical situation where the patient may starve from lack of nutrition.

Therefore, there appears a need in the art for a securing device that securely engages the connection member of a feeding set to the external retention member of a low profile gastrostomy tube so that inadvertent removal of the connection member is prevented.

SUMMARY OF THE INVENTION

In brief summary, the present invention overcomes and substantially alleviates the deficiencies in the prior art by providing a low profile gastrointestinal tube feeding system having a securing device for securing a feeding set to a low profile gastrostomy tube thereof disposed inside the viscera of a patient's body so that inadvertent removal of the feeding set from the gastrostomy tube is prevented. The low profile gastrostomy tube feeding system of the present invention is designed to pass through an opening or stoma formed through the wall of the abdomen and stomach or other viscera of a patient. The low profile gastrostomy tube comprises an external retention member which includes a body having opposing legs with an axial passage formed through the body between the two legs. The passage includes a distal opening and a proximal opening. The proximal opening of the external retention member is connected to a hollow tubular member having a distal end and a proximal end with a lumen formed between the ends. The distal end of the tubular member is connected to the proximal opening of the external retention member, while the proximal end of the tubular member is attached to an internal retention member disposed inside the patient's stomach or other hollow body organ. The internal retention member comprises a plurality of flexible retaining arms which, in its preset enlarged shape, retains the internal retention member inside the patient by anchoring the retention member to the body organ wall. A connection member, or adapter, is provided with the feeding set for attaching the feeding set to the low profile gastrostomy tube. The connection member includes a first opening set at a perpendicular angle to a second opening with a lumen formed between the openings. The perpendicular shape of the lumen permits the elongated tube to be attached to the connection member in such a manner that the elongate tube presents a low profile along the patient's body. The second opening of the connection member is attached to the distal opening of the external retention member of the low profile gastrostomy tube. The external retention member provides a means for preventing the low profile gastrostomy tube from inadvertently slipping into the patient's body by using the external retention member as an anchor that retains the distal end of the gastrostomy tube to the outer surface of a patient's abdominal wall. The hollow elongate tube includes first and second ends with a lumen formed between the ends that provides a conduit that supplies nutritional fluid directly to the patient's stomach through the low profile gastrostomy tube disposed therein. The first end of the elongate tube is connected to a source of nutrition, while the second end of the tube is connected to the first opening of the connection member attached to the external retention member. Finally, a securing device is provided for securing the connection member to the external retention member in order to prevent inadvertent removal of the connection member from the external retention member without first physically removing the securing device.

The securing device comprises a body having a top portion, middle portion and bottom portion. The inner surface of the top portion forms a locking tab adapted for engaging and retaining the connection member. The middle portion of the securing device forms an aperture adapted for slidably engaging the elongate tube therethrough, while the bottom portion forms opposing arms which engage grooves formed between the passage and the legs of the external retention member. A retention area adapted for retaining the top portion of the connection member there between as the arms of the bottom portion are concurrently engaging the external retention member is defined between the locking tab and the middle portion of the securing device. During manufacturing, the elongate tube is inserted through the aperture of the securing device so that the securing device slides along the elongate tube. The method for engaging the securing device to the connection member and the external retention device comprises the steps of sliding the securing device along the elongate tube until the opposing arms of the securing device begin to engage respective grooves of the external retention member. As the opposing arms engage the grooves, the locking tab concurrently engages the top outer surface of the connection member which is attached to the external retention member. The locking tab rides over the top outer surface of the connection member until the connection member falls behind the locking tab and becomes recessed in the retention area between the locking tab and the middle portion of the securing device. As the connection member is secured by the locking tab, the arms of the securing device concurrently engage the grooves of the external retention member until the arms are fully inserted therethrough. Thus, the connection member and the external retention member are secured to one another through the securing device which prevents inadvertent disconnection of the connection member from the external retention member without first disengaging the securing device from either the connection member or the external retention member.

Accordingly, the primary object of the present invention is to provide a securing device for securing a feeding set attached to a low profile gastrostomy tube.

Another object of the present invention is to provide a securing device that secures a feeding set to a low profile gastrostomy tube so that the feeding set cannot be inadvertently removed from the gastrostomy tube without first physically removing the securing device from either the feeding set or the gastrostomy tube. A further object of the present invention is to provide a securing device adapted to simultaneously engage and secure both the feeding set and a low profile gastrostomy tube.

These and other objects of the present invention are realized in the preferred embodiment of the present invention, described by way of example and not by way of limitation, which provides for a securing device for a low profile gastrointestinal feeding system that prevents inadvertent removal of the feeding set from the low profile gastrostomy tube.

Additional objects, advantages and novel features of the invention will be set forth in the description which follows, and will become apparent to those skilled in the art upon examination of the following more detailed description and drawings in which like elements of the invention are similarly numbered throughout.

DETAILED DESCRIPTION OF THE INVENTION

Figure 1:
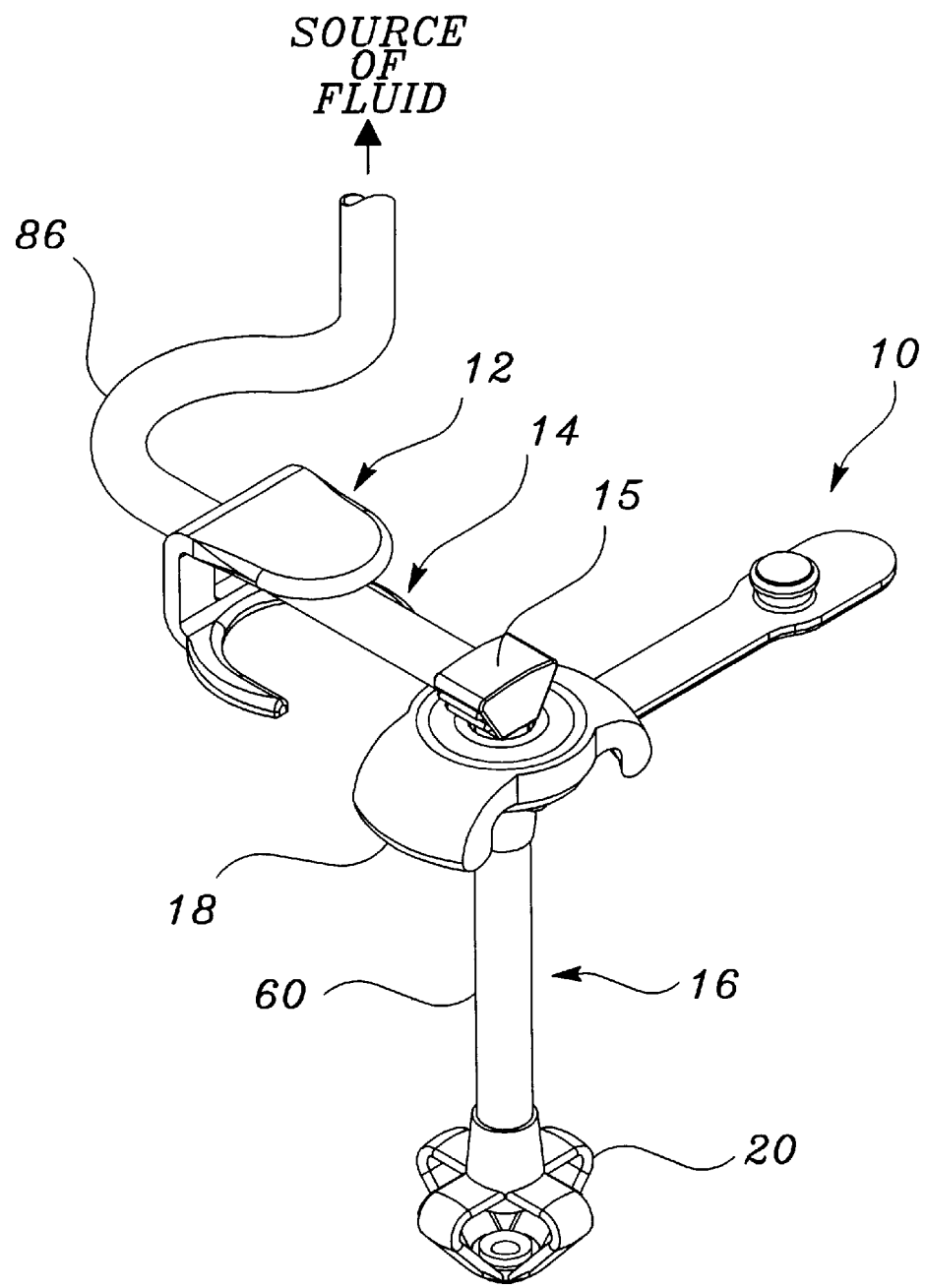
FIG. 1 is a perspective view of the low profile gastrointestinal feeding system showing the securing device slidably engaged along the elongate tube according to the present invention.
Figure 2:
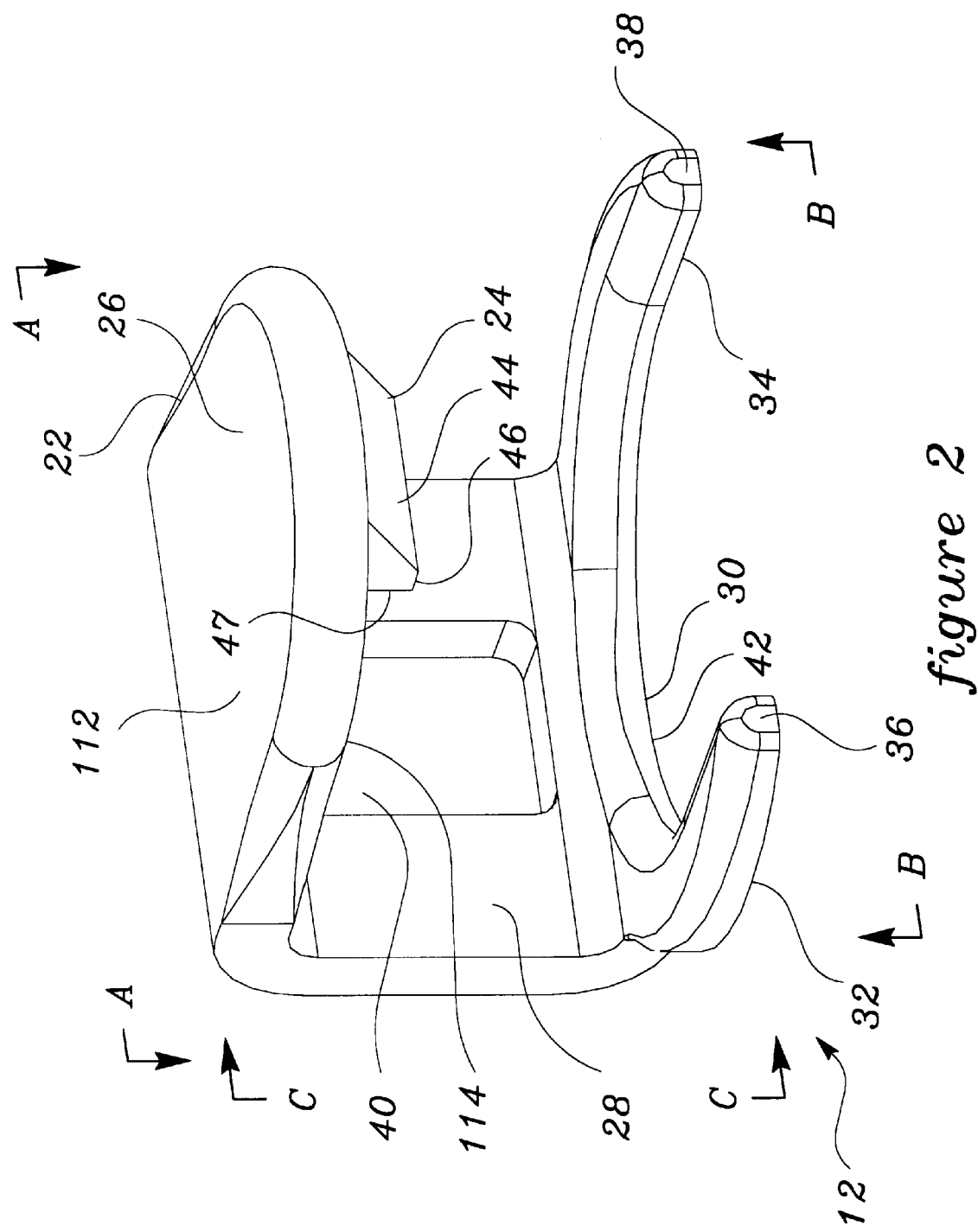
FIG. 2 is a perspective view of the securing device according to the present invention.
Figure 3:
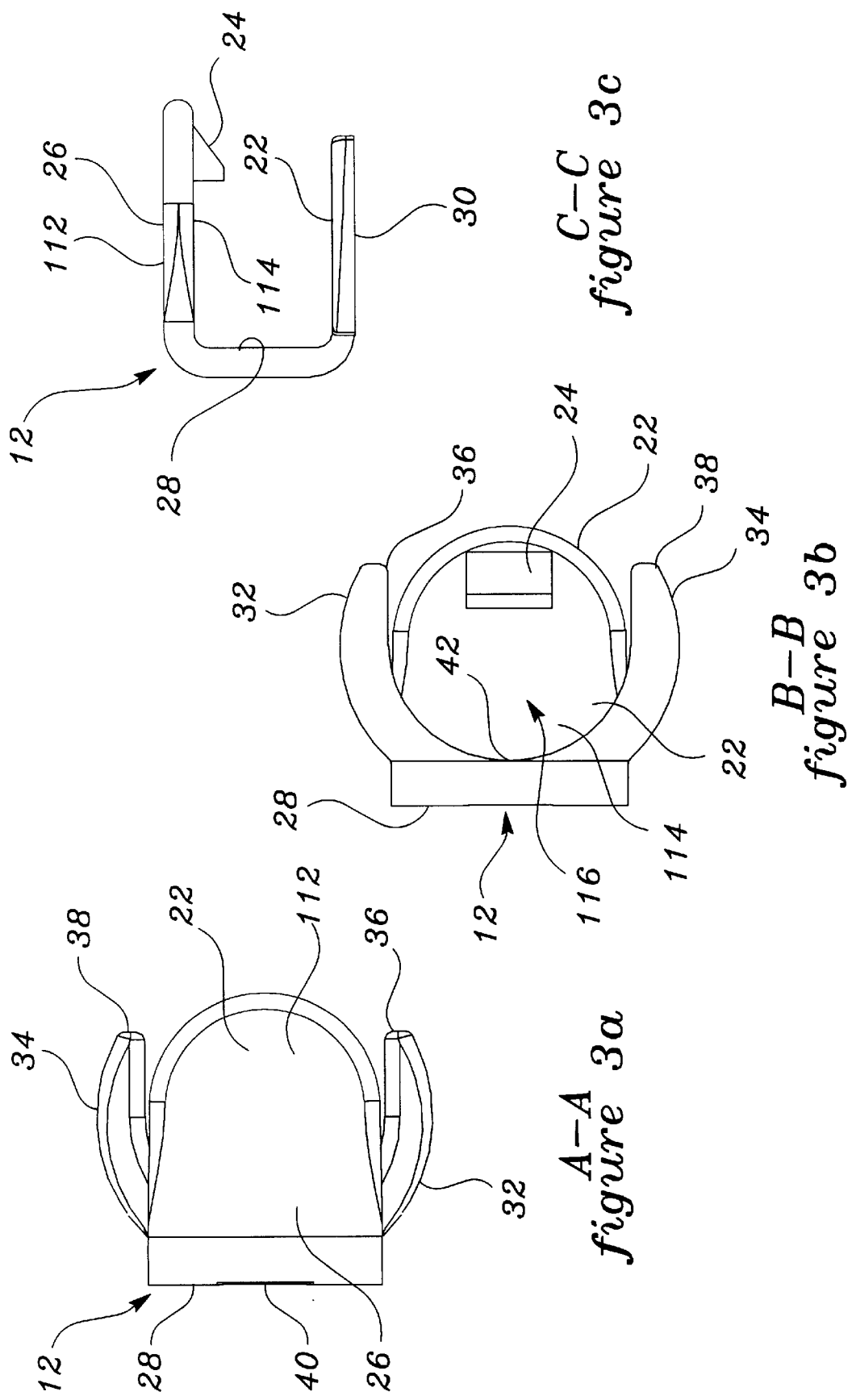
FIG. 3A is a top view of the securing device along line A—A shown in FIG. 2 according to the present invention.
FIG. 3B is a bottom view of the securing device along line B—B shown in FIG. 2 according to the present invention.
FIG. 3C is a side view of the securing device along line C—C shown in FIG. 2 according to the present invention.

Referring to the drawings, the preferred embodiment of the low profile gastrointestinal feeding system according to the present invention is illustrated and generally indicated as 10 in FIG. 1. The low profile gastrointestinal tube feeding system 10 comprises a feeding set 14 attached to a low profile gastrostomy tube 16. The gastrostomy tube 16 includes a tubular member 60 having an external retention member 18 attached at one end and an internal retention member 20 attached at the other end thereof.

Figure 6:
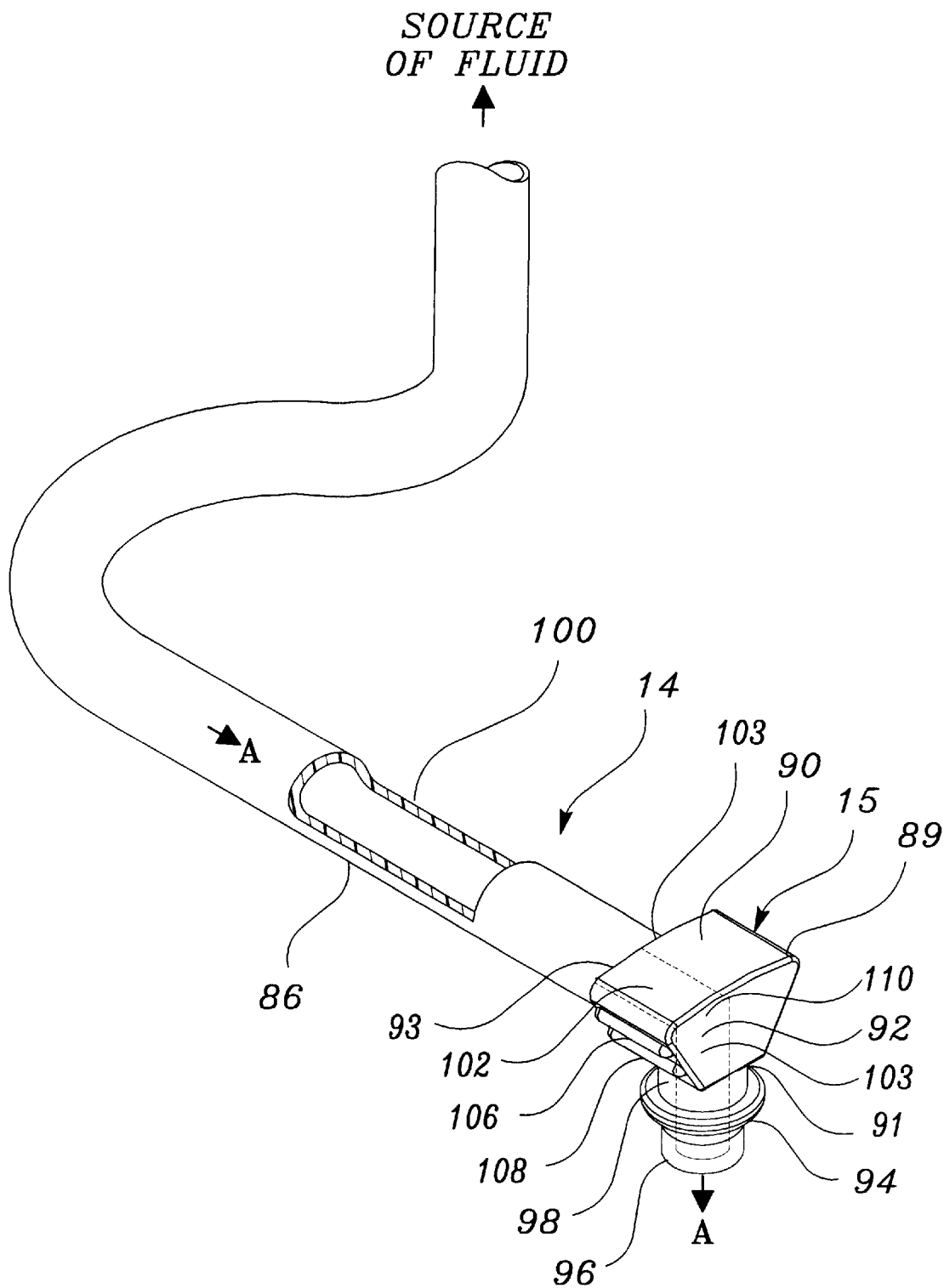
FIG. 6 is an isolated fragmentary perspective view of the elongate tube attached to a connection member according to the present invention.

Referring to FIG. 6, an isolated view of the feeding set 14 is shown. Feeding set 14 comprises a hollow elongate tube 86 with a lumen 100 shown in partial fragmentary section formed through tube 86 having a first end (not shown) and a second end 103. First end of elongate tube 86 is attached to a source of fluid, for example nutritional supplement, to be supplied to the patient through the low profile gastrostomy tube 16, while the second end 103 is attached to a connection member 15. The connection member 15 has a body 89 that includes opposing side grip portions 106 adapted to be gripped between a user's thumb and forefinger when attaching the connection member 15 to either the elongate tube 86 or the low profile gastronomy tube 16. The body 89 further includes opposing top and bottom portions 90, 91 and opposing front and back portions 92, 93. A horizontal lumen 102 forms a passage through one portion of body 89 and merges with vertical lumen 103 that meets lumen 102 at approximately a 90-degree angle at an elbow 110. Lumens 102, 103 establish a fluid pathway though connection member 15 for the passage of fluid to the low profile gastrostomy tube 16 from the elongate tube 86. A tubular-shaped vertical extension member 98 extension outwardly from the bottom portion 91 of body 89 along the same downward vertical orientation as lumen 103. An annular retaining flange 94 is formed around extension member 98 and provides a means of attaching connection member 15 to external retention member 18, as shall be explained in greater detail below. Thus, connection member 15 functions as a 90-degree adapter for connecting elongate tube 86 to the external retention member 18 at a low profile in relation to the patient's body.

Referring to FIGS. 1, 2 and 3A–3C, a securing device 12 according to the present invention is illustrated and provides a means for securing the connection member 15 to the external retention member 18 after attachment of the connection member 15 thereto. The securing device 12 includes a body 22 that forms a top portion 26, back portion 28 and lower portion 30. The top portion has a flat outer surface 112 and an inner surface 114 which is in opposed relation to the lower portion 30 and includes a locking tab 24 for engaging and securing the securing device 12 to the connection member 15. Locking tab 24 includes a beveled forward part 44, a flat middle part 46 and a straight back part 47. Beveled forward part 44 forms an angled portion adapted to initially engage and ride over the rear part 93 of connection member 15. A retention area 116 is provided along inner surface 114 between the back portion 28 and the locking tab 24 of securing device 12 for securely engaging device 12 to connection member 15. The back portion 28 of securing device 12 forms an aperture 40 adapted to slidably engage the elongate tube 86 therethrough, while the lower portion 30 forms opposing arms 32, 34 having respective distal tips 36, 38 which are adapted to engage the external retention member 18. Preferably, opposing arms 32, 34 collectively form a generally curved configuration with arms 32, 34 meeting at an apex 42 located in the middle of back portion 28. However, opposing arms 32, 34 can also form a generally straight parallel configuration.

Figure 4:
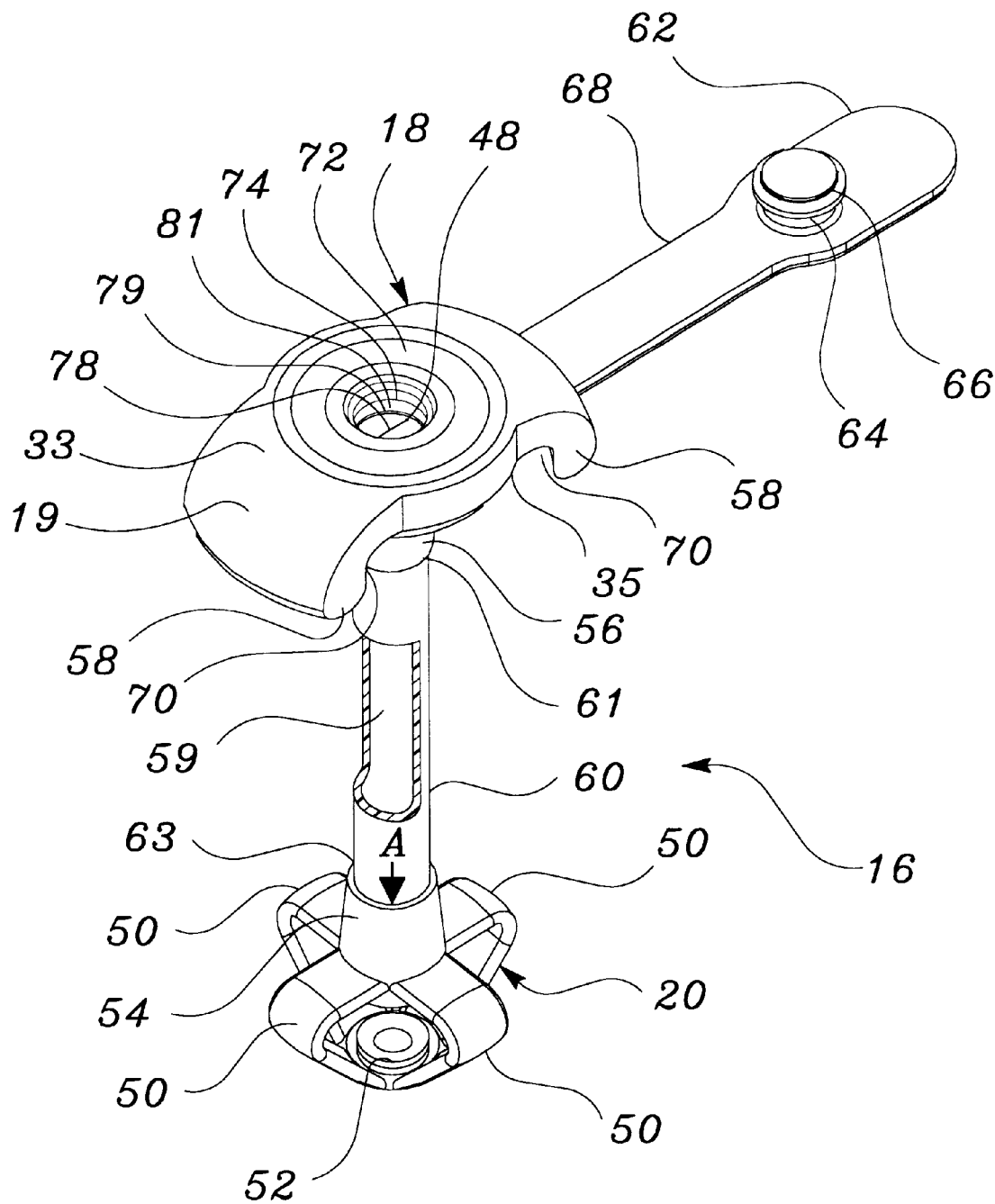
FIG. 4 is an elevated perspective view showing the low profile gastrostomy tube according to the present invention.

Referring to FIG. 4, an isolated perspective view of the low profile gastrostomy tube 16 is shown. The external retention member 18 includes a body 19 comprising a top surface 33 and a bottom surface 35. The bottom surface 35 forms opposing legs 58 adapted to be seated against the outer abdominal wall of a patient and to also serve to retain and anchor the external retention member 18 thereto when the low profile gastrostomy tube 16 is inserted into a patient' body. The top surface 33 includes an axial passageway 79 through body 19 having a distal opening 81 formed at top surface 33 and a proximal opening 83 (FIG. 7) formed at bottom surface 35. An annular undercut 74 is formed around the circumference of passageway 79 near the distal opening 81 for engaging either an annular flange 66 of cap member 64 for sealing off passageway 79 or retaining flange 94 for attaching the connection member 15 to the external retention member 18 and establishing fluid flow communication between the source of nutrition and the low profile gastrostomy tube 16. The engagement of either flange 66 or flange 94 with undercut 74 is preferably a snap fit engagement. However, in the alternative an interference fit or a combination of interference and snap fit engagement is felt to fall within the scope of present invention. Passageway 79 further includes a valve member 48 spaced below undercut 74 and disposed across passageway 79. Valve member 48 comprises an impermeable barrier having one or more slits 78 which provide an anti-reflux action that prevents fluid from flowing in a direction opposite that of fluid pathway A illustrated in FIGS. 5 and 7. Affixed or integrally formed with the external retention member 18 is a tethered cap 62 which includes a tether 68 which attaches cap member 64 to external retention member 18. Cap member 64 has an annular flange 66 adapted to engage undercut 74 when sealing distal opening 81 of passageway 79. Annular undercut 74 is spaced above and concentrically around valve member 48.

Top surface 33 of external retention member 18 also includes a retaining ring 72 which surrounds valve member 48 and provides a protective reinforcing structure around valve member 48 against manual deformation. An upper socket 56 is integrally formed with or attached to the proximal opening 82 of external retention member 18 at one end and integrally formed with or attached to the tubular member 60 at the other end thereof.

Figure 8:
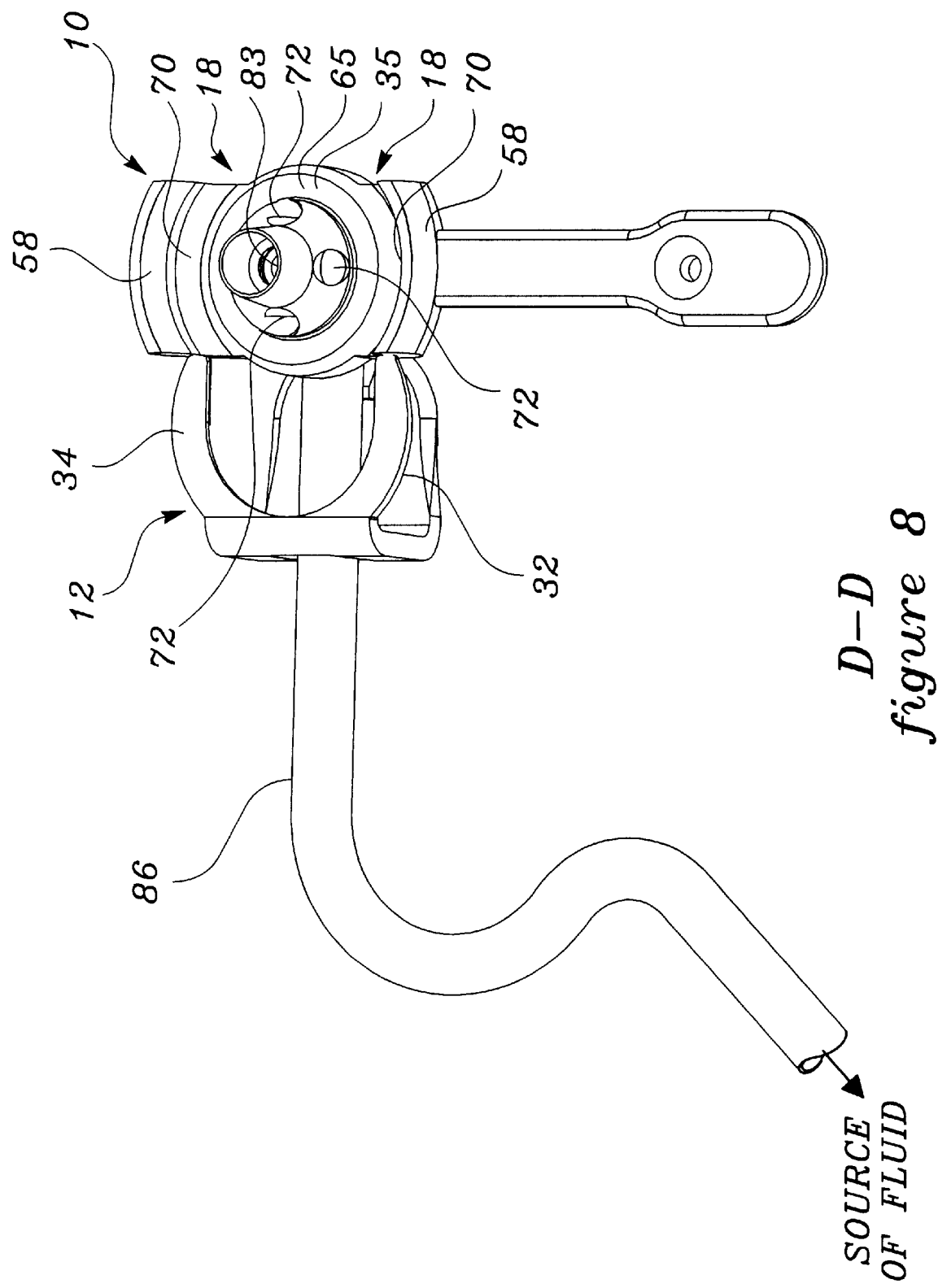
FIG. 8 is an isolated partial bottom view of the low profile gastrointestinal feeding system along line D—D shown in FIG. 7 according to the present invention.

A bottom view of the external retention member 18 is illustrated in FIG. 8. The bottom surface 35 of external retention member 18 includes an annular body 65 and two generally opposing grooves 70 which are formed between respective legs 58 and annular body 65. Opposing grooves 70 have a generally curved configuration adapted to engage and secure respective arms 32, 34 of securing device 12 when device 12 is secured to the external retention member 18 and connection member 15, as shall be discussed in greater detail later. A plurality of reinforcing members 76 surround annular body 65 and provide structural reinforcement.

Referring back to FIG. 4, tubular member 60 comprises a lumen 59 shown in partial fragmentary section having a distal end 61 and a proximal end 63. One end of a lower socket 54 is integrally formed with or attached to the proximal end 63 of tubular member 60, while the upper socket 56 is integrally formed with or attached to the distal end 61 of tubular member 60, thereby securing member 60 between the external retention member 18 retained outside the patient and the internal retention member 20 anchored inside the patient. Tubular member 60 provides a conduit for fluid pathway A for delivery of fluid into the patient's stomach or other viscera.

The other end of lower socket 54 is integrally formed with or attached to the internal retention member 20. Internal retention member 20 comprises a plurality of flexible retaining arms 50 with each arm 50 including a hinge 51 for flexing the internal retention member 20 into a pre-set enlarged shape illustrated in FIG. 4 that prevents the retention member 20 from being withdrawn through the stoma of a patient. The upper part of the retaining arms 50 meet at the lower socket 54 at one end and a grommet 50 formed at the other end. The grommet 50 serves as a fastening support for seating the obturator rod (not shown) during insertion of the low profile gastrostomy tube 16. The method for inserting and anchoring the low profile gastrostomy tube 16 using the obturator rod is disclosed in the above referenced U.S. Pat. No. 5,248,302 to Patrick et al.

Figure 5:
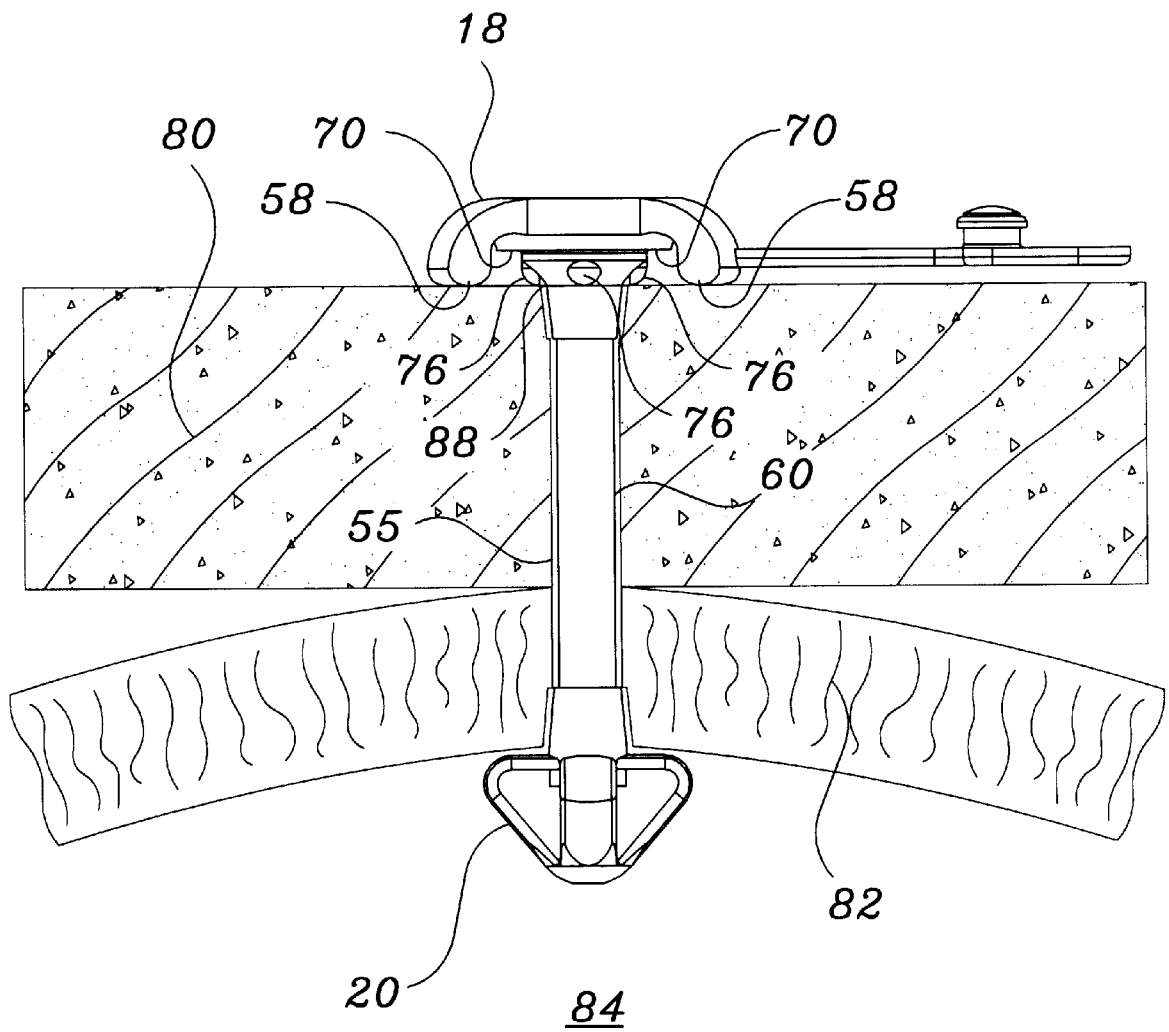
FIG. 5 is an isolated side view of the low profile gastrostomy tube passed through an opening in the viscera of a patient according to the present invention.

Referring to FIG. 5, an isolated side view of the low profile gastrostomy tube 16 is shown with the tubular member 60 inserted through a stoma 88 and into the stomach 84 or other viscera of a patient by via passage 55 formed through the abdominal wall 80 and stomach wall 82 of a patient. The internal retention member 20 attached to the tubular member 60 is shown in its pre-set enlarged position which anchors retaining arms 50 against the stomach lining 82 and prevents withdrawal thereof through passage 55. Conversely, the external retention member 18 attached to the distal end 61 of tubular member 60 prevents tubular member 60 from inadvertently slipping into passage 55.

Figure 7:
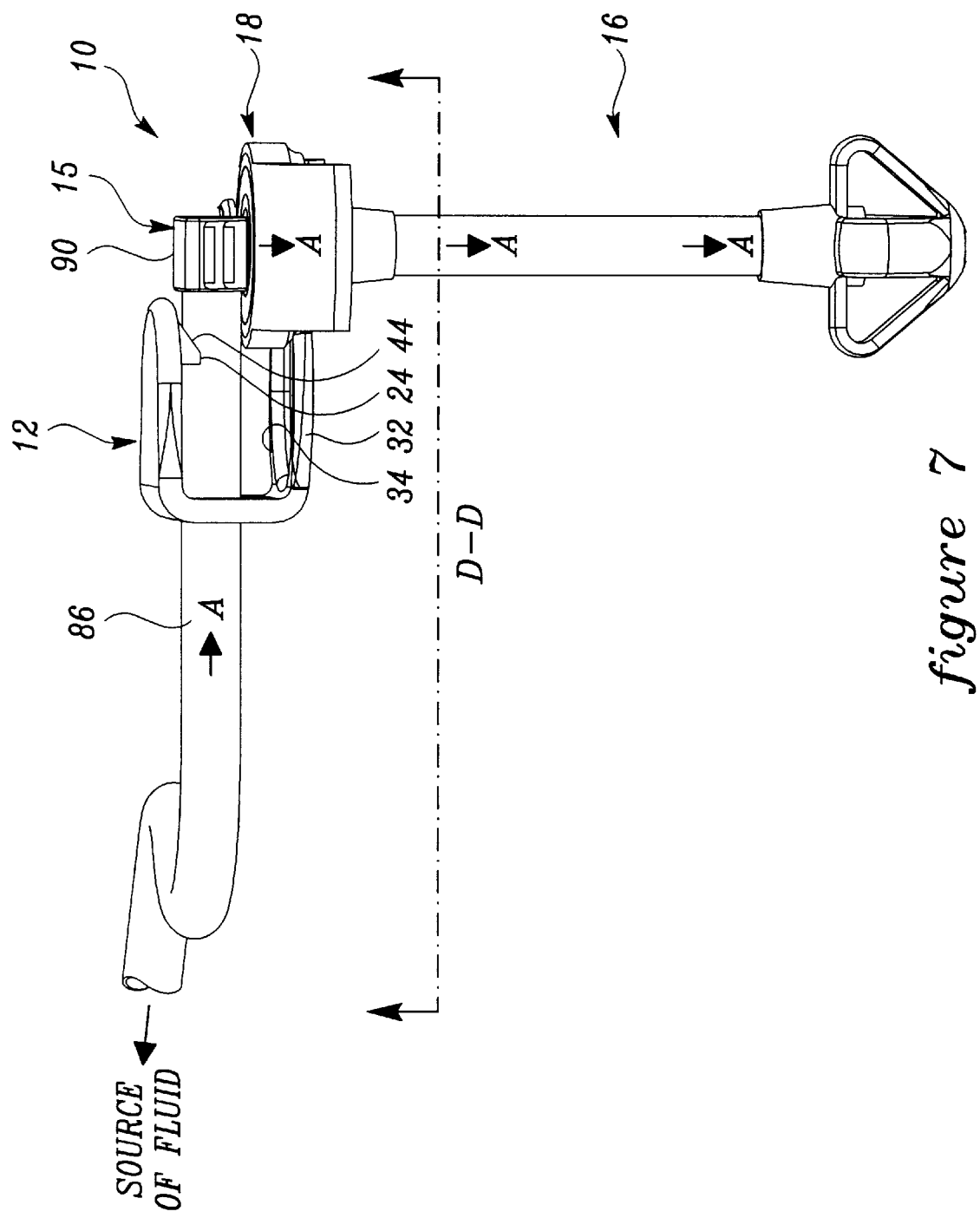
FIG. 7 is a side view of the low profile gastrointestinal feeding system showing the securing device in a pre-engagement position according to the present invention.

The method for engaging the securing device 12 to both the connection member 15 and the external retention member 18 once the low profile gastrostomy tube 16 has been properly inserted into a patient is illustrated in the sequence of positions shown in FIGS. 7–12. Referring to FIGS. 7 and 8, the pre-engagement position of the securing device 12 is shown as device 12 is slidably engaged along elongate tube 86 toward connection member which is attached to external retention member 18.

In the pre-engagement position, arms 32, 34 of securing device 12 are generally aligned with respective grooves 70 of external retention member 18. As the arms 32, 34 are aligned with grooves 70, the locking tab 24 of securing device 12 is also aligned with the top portion 90 of connection member 15. As the user slides the securing device 12 forwardly toward the external retention device 18, each of tips 36, 38 engage respective grooves 70 of the external retention member 18, while the beveled forward part 44 of locking tab 24 concurrently engages the top portion 90 of connection member 15.

Figure 9:
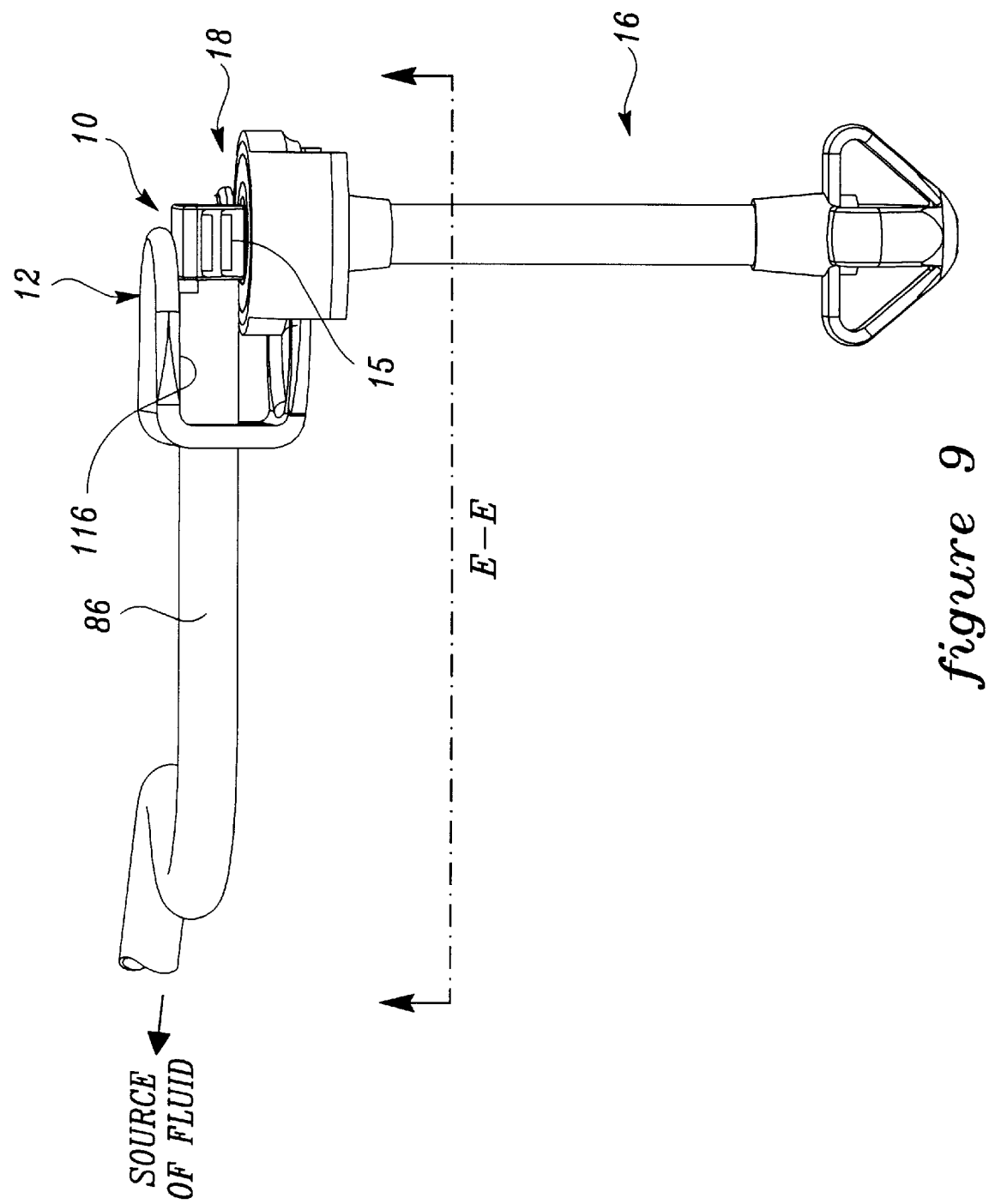
FIG. 9 is a side view of the low profile gastrointestinal feeding system showing the securing device in the engaging position according to the present invention.
Figure 10:
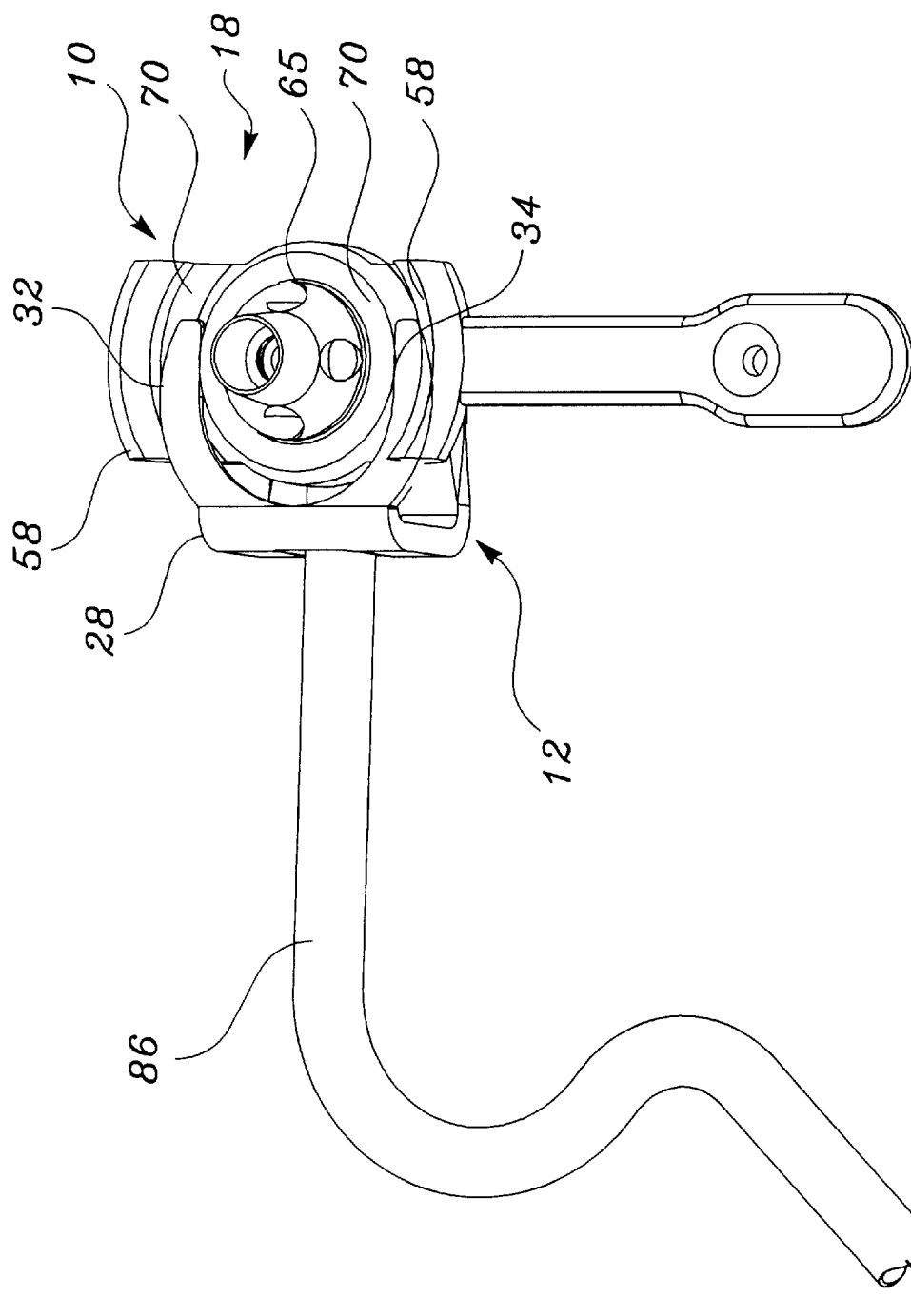
FIG. 10 is an isolated partial bottom view of the low profile gastrointestinal feeding system along line E—E shown in FIG. 9 according to the present invention.

In the engaging position shown in FIGS. 9 and 10, tips 36 and 38 have sufficiently entered into grooves 70 so that arms 32, 34 begin to flex as arms 32, 34 follow the slightly curved path formed by respective grooves 70. As arms 32, 34 engage respective grooves 70 the top portion 90 of connection member 15 rides under the beveled forward part 44 of locking tab 24 until portion 90 rides under flat middle part 46.

Figure 11:
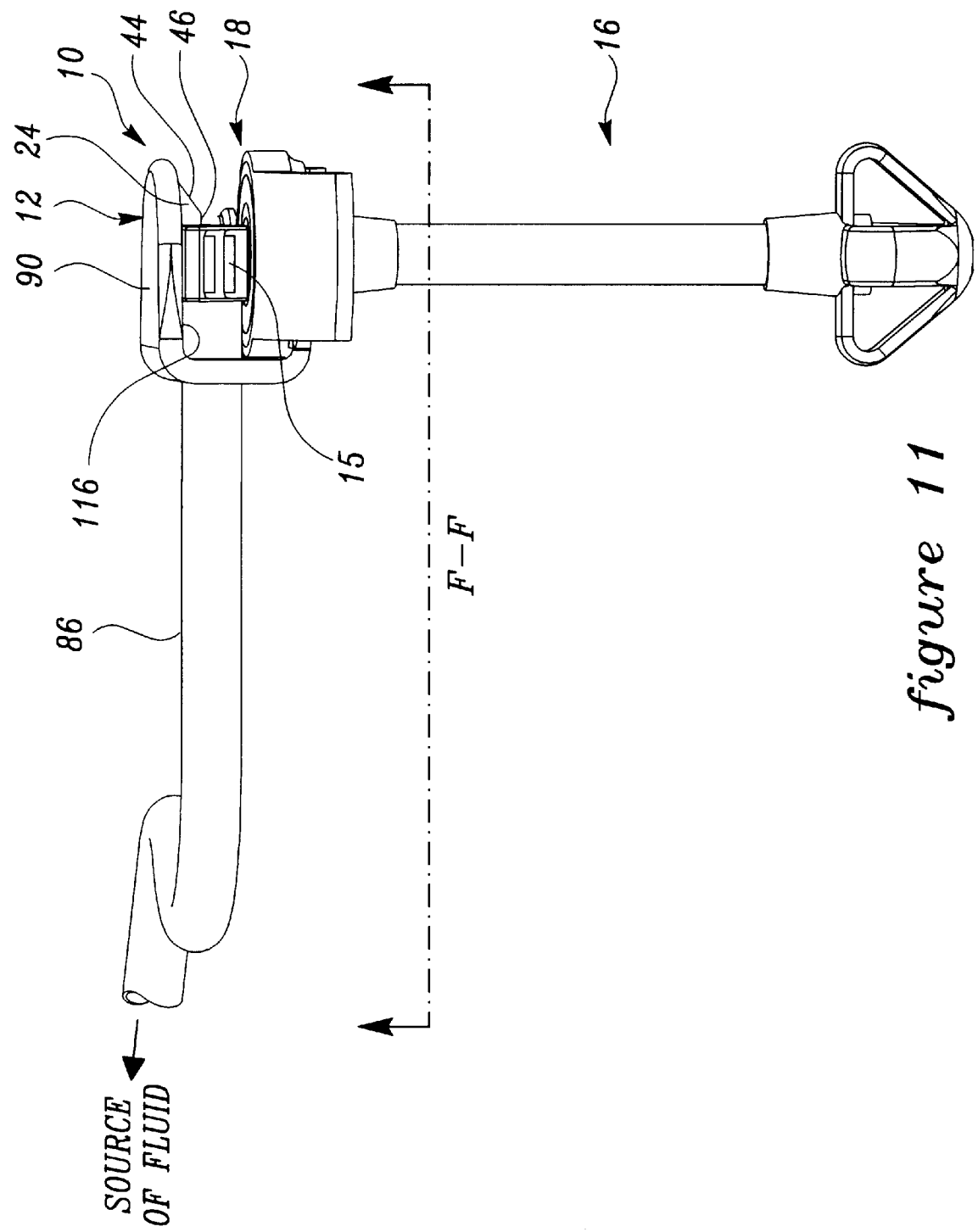
FIG. 11 is an isolated side view of the low profile gastrointestinal feeding system showing the securing device in a post-engagement position according to the present invention.
Figure 12:
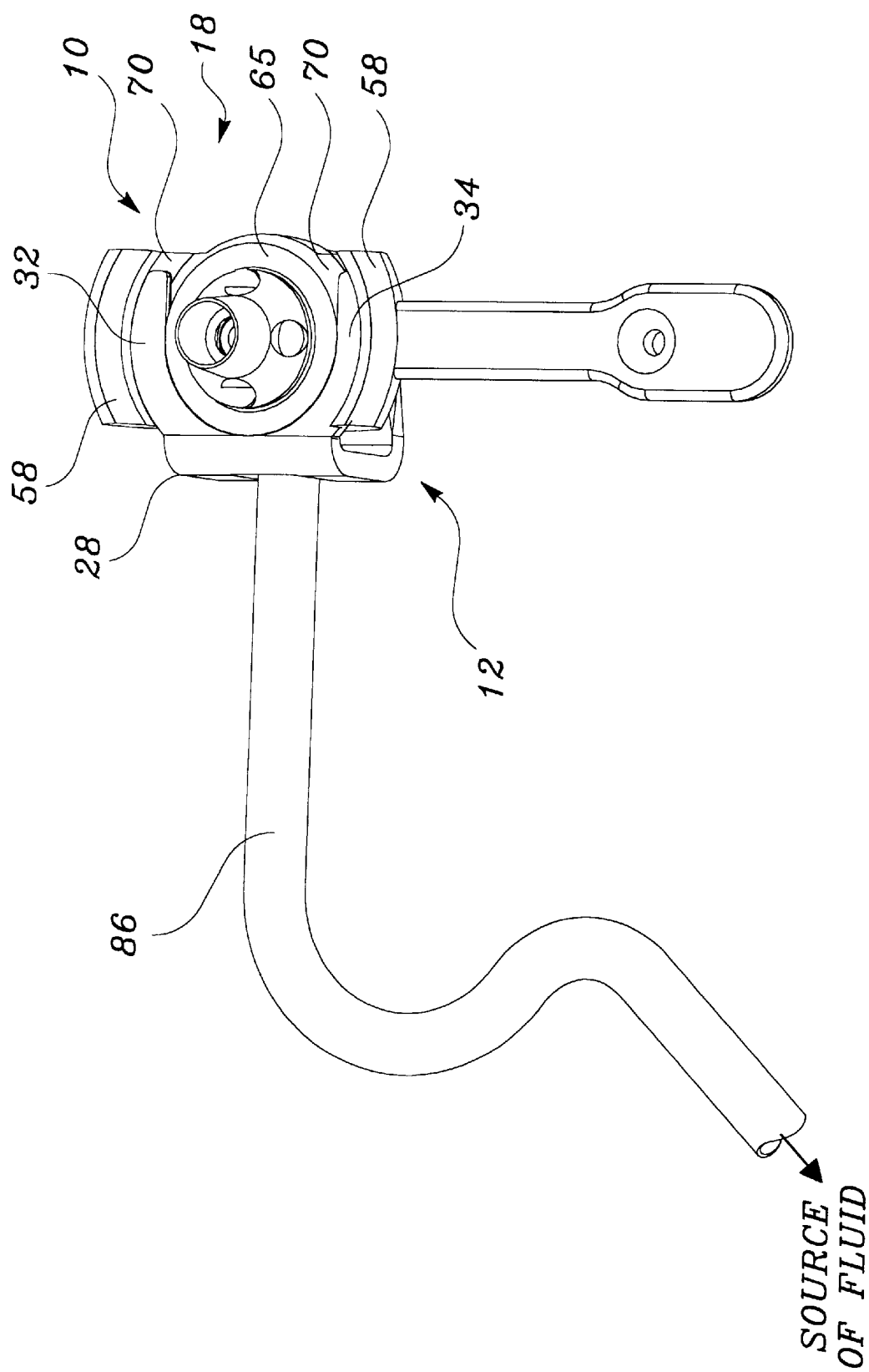
FIG. 12 is an isolated partial bottom view of the low profile gastrointestinal feeding system along line F—F shown in FIG. 11 according to the present invention.

In the post engagement position of securing device 12 shown in FIGS. 11 and 12, arms 32, 34 have fully engaged grooves 70. While arms 32, 34 become fully engaged in grooves 70, the front portion 90 of connection member 15 passes under the flat middle part 46, until front portion 90 falls behind part 46 and becomes recessed in retention area 116 formed between straight back part 47 and back portion 28 of securing device 12, thereby securely engaging the top portion 90 of device 12 to connection member 15. In the post engagement position, arms 32, 34 have become fully engaged within respective grooves 70 of external retention member 18 and the top portion 90 of connection member 15 is full recessed within retention area 116, thereby fully securing connection member 15 to external retention member 18 to the top and bottom portions 26, 30 of securing device 12. Neither the external retention member 18 nor the connection member 15 may be disengaged from one another without first physically disengaging the securing device 12 from either or both members 15 or 18.

Preferably, the securing device 12 is injection molded from polypropylene or other suitable medical-grade plastic that possesses sufficient flexibility and durability. However, in the alternative, stainless steel or other metal suitable for medical use is also felt to fall within the scope of the present invention.

It should be understood from the foregoing that, while particular embodiments of the invention have been illustrated and described, various modifications can be made thereto without departing from the spirit and scope of the present invention. Therefore, it is not intended that the invention be limited by the specification; instead, the scope of the present invention is intended to be limited only by the appended claims.

We claim:

1. A device designed to pass through an opening in the wall of the abdomen and stomach or other viscera of a patient, said device comprising:
    a feeding set, said feeding set including an elongate tube having one end attached to a source of fluid and another end attached to a connection member;
    a feeding tube including a tubular member disposed inside the opening of a patient and interposed between an external retention member seated on the outside of a patient and an internal retention member anchored inside the viscera of a patient, said connection member being attachable to said external retention member for establishing fluid flow communication between said source of fluid and a patient; and
    a securing member having opposed portions and being slidably engaged along said elongate tube, one of said opposed portions securely engaging said connection member and the other of said opposed portions securely engaging said external retention member, whereby said connection member cannot be disengaged from said external retention member without first detaching one of said opposing portions of said securing device from either said connection member or said external retention member.

2. The device according to claim 1, wherein said external retention member includes a body, said body forming a passage therethrough and two opposing legs, said two opposing legs forming respective grooves between each of said legs and said passage.

3. The device according to claim 1, wherein said one of said opposing portions of said securing member includes two opposing arms and an aperture formed therebetween.

4. The device according to claim 1, wherein said securing member further includes an aperture interposed between said opposing portions.

5. The device according to claim 4, wherein said elongate tube slidably engages said securing member through said aperture of said securing member.

6. The device according to claim 3, wherein said two opposing arms of said securing member are adapted to securely engage said respective grooves of said external retention member when said securing member simultaneously engages said connection member and said external retention member.

7. The device according to claim 1, wherein said one of said opposed portions of said securing member includes a retention portion, said retention portion adapted to securely engage said connection member when said securing member is simultaneously engaged to said connection member and said external retention member.

8. The device according to claim 1, wherein a fluid pathway is established between said source of fluid and the free end of said tubular member.

9. The device according to claim 1, wherein said elongate tube attaches to said connection member at a perpendicular relationship with respect to said tubular member.

10. A device designed to pass through an opening in the wall of the abdomen and stomach or other viscera of a patient, said device comprising:

an external retention member including a body, said body forming a passage therethrough, said passage having a distal opening and a proximal opening;

a tubular member having a distal end and a proximal end with a first lumen formed therebetween, said distal end connected to said proximal opening of said passage;

an internal retention member connected to said proximal end of said tubular member for retaining said internal retention member inside a body organ;

a connection member that includes a first opening and a second opening with a second lumen formed therebetween, said second opening adapted for connection with said distal opening of said external retention member;

an elongate tube having a first end and a second end with a third lumen formed therebetween, said first end connected to a source of fluid and said second end connected to said first opening of said connection member; and a means for simultaneously securing said connection member to said external retention member in such a manner that neither said connection member nor said external retention member may be disengaged from one another without first disengaging said securing device from either said connection member or said external retention member.

11. A method for securing a connection member attached to a hollow external retention member of an internal anchoring device, the internal anchoring device including a hollow tubular member having opposing ends, the tubular member being designed to pass through the wall of the abdomen and stomach or other viscera of a patient, one end of the tubular member is attached to a hollow internal retention member disposed inside the patient, while the other end of the tubular member is attached to the external retention member retained outside of a patient, the external retention member having one end attachable to the connection member, the connection member including a first opening and a second opening with a first lumen formed therebetween, the first opening being attachable to an elongated tube, the elongated tube having a first end and a second end with a third lumen formed therebetween, the first end connected to a source of fluid and the second end connected to the first opening of the connection member such that fluid flow communication is established between the source of fluid and the internal retention device, and a securing member being slidably engaged along the elongated tube, said securing member including opposed retaining portions for simultaneously retaining the connection member and the external retention member together, the steps of the method comprising:

a) engaging the connection member to the external retention member;

b) establishing fluid flow communication between the source of fluid and the internal retention member;

c) grasping the securing member and sliding the securing member along the elongated tube until one of said opposed retaining portions engages the connection member while the other of said opposed retaining portion engages the external retention member; and d) securing one of said opposed retaining portions to the connection member while securing the other of said opposed retaining portions to the external retention member such that the connection member cannot be disengaged from the external retention member without first disengaging at least one of said opposed retaining portions.

12. A securing member adapted to slidably engage along an elongate tube for securing a feeding set to a feeding tube disposed inside the viscera of a patient comprising:

a body having opposed retention portions, one of said opposed retention portions being securely engageable to said feeding set and the other of said opposed retention portions being securely engageable to said feeding tube, so that the feeding set is simultaneously secured to said feeding tube by said securing member.

13. The securing member according to claim 12, wherein said one of said opposed retention portions includes a tab section adapted to securely engage said connection member to said securing member.

14. The securing member according to claim 12, wherein said other of said opposed retention portions engageable to said external retention member includes a pair of opposing arms, said pair of opposing arms being adapted to securely engage said external retention member to said securing member.

15. The securing member according to claim 14, wherein said external retention member defines a pair of grooves adapted to engage said opposing arms therethrough.

16. The securing member according to 12, wherein said connection member cannot be disengaged from said external retention member without first disengaging at least one of said retaining portions from said connection member and said external retention member.

* * * * *